United States Patent [19]

Shlenker

[11] Patent Number: 4,771,482

[45] Date of Patent: Sep. 20, 1988

[54] GLOVE FOR INHIBITING THE SPREAD OF CONTAGIOUS DISEASES AND METHOD OF USING THE SAME

[76] Inventor: Robin R. T. Shlenker, 2165 E. Alameda Ave., Denver, Colo. 80209

[21] Appl. No.: 74,629

[22] Filed: Jul. 17, 1987

[51] Int. Cl.$^4$ ............................................. A41D 19/00
[52] U.S. Cl. ...................................... 2/161 R; 2/159; 2/168
[58] Field of Search ............... 2/161 R, 159, 163, 164, 2/167, 168

[56] References Cited

U.S. PATENT DOCUMENTS

| | | |
|---|---|---|
| 1,954,262 | 4/1934 | Potter ....................................... 2/159 |
| 2,410,460 | 11/1946 | Robinson . |
| 2,792,835 | 5/1957 | Ferguson . |
| 3,110,035 | 11/1963 | La Hue ..................................... 2/168 |
| 3,121,877 | 2/1964 | Gintner . |
| 3,342,182 | 9/1967 | Charos .............................. 2/16 R X |
| 3,633,216 | 1/1972 | Schonholtz ............................. 2/168 |
| 3,672,351 | 6/1972 | Ubersax . |
| 3,911,501 | 10/1975 | Seltzer ................................. 2/168 X |
| 3,975,775 | 8/1976 | Alsop .................................. 2/168 X |
| 4,185,330 | 1/1980 | Stager . |
| 4,214,321 | 7/1980 | Nuwayser . |
| 4,471,538 | 9/1984 | Pomeranz . |

FOREIGN PATENT DOCUMENTS 540241 10/1941 United Kingdom .

Primary Examiner—Louis K. Rimrodt
Assistant Examiner—J. L. Olds

[57] ABSTRACT

A glove for inhibiting the spread of contagious diseases such as AIDS and Hepatitis to a person handling the body fluid of a person infected with the disease. The glove is flexible, stretchable, and relatively thin, and includes at least one layer of relatively thin pockets or chambers containing a sterilizing fluid capable of sterilizing the microbes that produce the disease. If an object cuts through the glove and into a person's hand, the sterilizing fluid will be released to help sterilize the infectious microbes in the region around the cut so that the microbes are rendered ineffective either before reaching the person's hand, after reaching the person's hand, or both. A method of using the glove for medical operaitons is also disclosed.

37 Claims, 1 Drawing Sheet

GLOVE FOR INHIBITING THE SPREAD OF CONTAGIOUS DISEASES AND METHOD OF USING THE SAME

BACKGROUND OF THE INVENTION

There are a number of contagious diseases that can be spread by passing infectious agents or microbes from one person's blood or other infective body fluid to another person's blood or other body fluid. Two of the most feared diseases that can be spread in this manner are Hepatitis and Acquired Immunodeficiency Syndrome, otherwise known as AIDS. Often, one must touch, handle or otherwise come in contact with a person's body fluid either knowing that the person has a disease such as AIDS or without an opportunity to adequately determine whether the person has such a disease. For example, doctors and nurses must treat patients and perform surgical operations on patients sometimes knowing that the person has a contagious disease or during an emergency situation when there is no opportunity to determine whether the person has such a disease. Similarly, policemen and ambulance workers must often handle and treat persons involved in automobile accidents, shootings, and the like without an opportunity for determining whether the person has a contagious disease.

Doctors, dentists, medical technologists, and nurses protect against the transmission of contagious diseases in the work place and during invasive procedures by wearing conventional flexible, stretchable, disposable, sterile latex gloves. Such latex gloves are usually powdered on the inside with talc or a similar material to help keep the glove interior dry and to facilitate removal of the glove. A decision was recently made to equip the Denver, Colo. police force with such latex gloves so that policemen could use the gloves in situations where they would contact another person's body fluids, such as at car accidents and shootings. While these conventional latex gloves provide a great degree of protection against the transmission of contagious diseases, such gloves can be torn, ripped, punctured or otherwise cut. The person's hand is often correspondingly cut immediately below the cut in the glove. For example, doctors often cut their fingers and hands with a scalpel during operations and sometimes puncture their fingers and hands with suture needles. Also, policemen might cut their hands on pieces of glass, jagged pieces of metal, and the like at car accident scenes. The frequency of such cuts is significant, and, when considering the fear of accidentally contracting diseases such as AIDS, constitutes a serious problem.

SUMMARY OF THE INVENTION

The present invention relates to a glove for inhibiting the spread of a contagious disease such as AIDS and Hepatitis to a person handling the body fluid of a person infected with the disease. The glove is flexible, stretchable, and relatively thin, and includes at least one layer of relatively thin pockets or chambers containing a fluid capable of sterilizing the microbes that produce the disease. If an object cuts through the glove and into a person's hand, the sterilizing fluid will be released to help sterilize the infectious microbes in the region around the cut so that the microbes are rendered ineffective either before reaching the person's hand, after reaching the person's hand, or both. A method of using the glove for medical operations is also disclosed.

BRIEF DESCRIPTION OF THE DRAWINGS

The invention will be described with reference to the accompanying drawings, wherein.

DESCRIPTION OF THE PREFERRED EMBODIMENT

Figure 1:
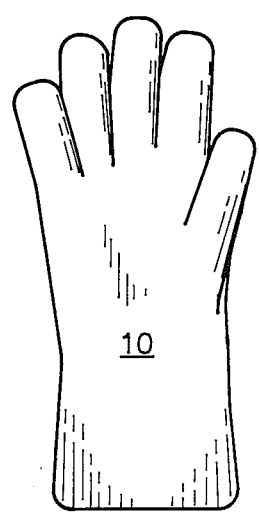
FIG. 1 is a plan view of a glove in accordance with one embodiment of the present invention.

Referring now to the drawings wherein like reference numerals and symbols refer to the same item, there is shown in FIG. 1 a glove 10 having a shape and configuration similar in all essential respects to the conventional latex gloves presently worn by doctors, dentists, and nurses. An example of a conventional latex glove is the "Perry" surgeon's glove manufactured by Smith & Nephew of Massillon, Ohio. The glove 10 of the present invention, however, possesses at least one pocket or chamber containing a fluid capable of sterilizing contagious disease-producing microbes.

Figure 4:
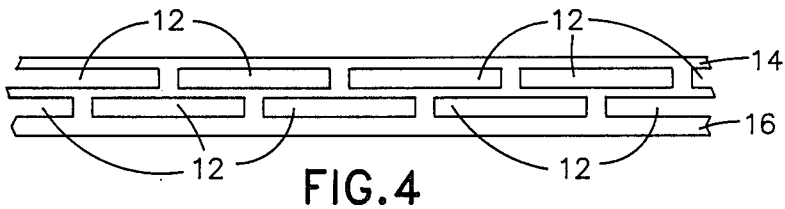
FIG. 4 is a schematic cross-sectional view of the gloves shown in FIGS. 1, 2 and 3 revealing two layers of chambers containing a sterilizing fluid.
Figure 5:
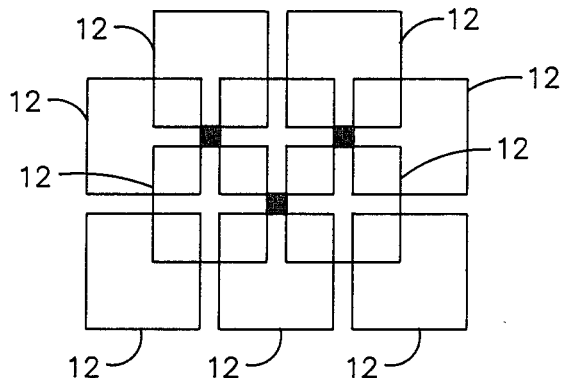
FIG. 5 is a top schematic illustration showing the staggered relation of the chambers in the two layers revealed in FIG. 4.

As best shown in FIGS. 4 and 5, the glove 10 preferably includes an array of thin, square-shaped chambers 12 arranged side by side in two layers. The chambers 12 in each layer are staggered with respect to the chambers 12 in the adjacent layer. Such staggering minimizes the possibility that a needle or similar object could puncture through the glove 10 and cut the person's hand without protruding through one of the chambers 12 and releasing the sterilizing fluid contained therein. As shown by the darkened areas in FIG. 5, the staggered arrangement of the two layers of chambers 12 results in a relatively minuscule potential area for a needle or similar object to puncture through the glove 10 and cut the person's hand without also puncturing the cavity 12. It should be readily appreciated that either a single layer of chambers 12 could be utilized or three layers of chambers 12 arranged in a staggered relationship could be effectively used and would insure that a needle or similar object could not puncture through the glove 10 and cut a person's hand without also puncturing a chamber 12. Also, although FIGS. 4 and 5 depict relatively thin, square-shaped chambers 12, a variety of different shapes and sizes of chambers 12 can be effectively used. For example, the chambers 12 might be relatively thin and circular shaped or diamond shaped. Moreover, although FIG. 4 depicts the chambers 12 as possessing squared or cornered ends, it should be appreciated that the ends may be curved or rounded.

The thickness of the glove 10 is preferably in the range of between one millimeter and five millimeters so that the flexibility and stretchability of the glove can be maintained and so that the glove 10 does not significantly diminish the sensitivity with which the person's hand touches and feels an object. Also, the outer sheath 14 of the glove 10 (that region of the glove disposed outwardly of the outer layer of chambers 12) is relatively thinner than the inner sheath 16 of the glove 10 (that region of the glove located inwardly of the inner layer of chambers 12). The relative thickness of the sheath 16 provides strength so that the inner sheath 16 might not be cut even though the outer sheath 14 is cut. A glove 10 constructed according to the depictions of FIGS. 4 and 5 preferably contains between 50 and 500 different chambers 12. Preferably the volume of each chamber is less than two cubic centimeters.

Figure 6:
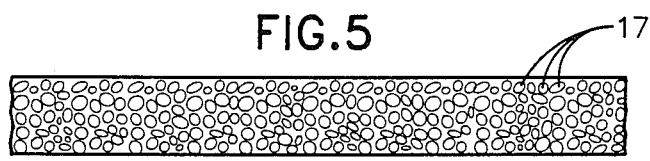
FIG. 6 is a schematic cross-sectional view of the gloves shown in FIGS. 1, 2 and 3 but possessing a different arrangement of the chambers.

A glove 10 according to the present invention can also be constructed somewhat like a sponge, with a plurality of tiny voids or chambers 17 that encapsulate the sterilizing fluid. Such a glove 10 construction is depicted in FIG. 6. Again, it should be appreciated that it would be virtually impossible to puncture through a glove 12 constructed with a host of chambers 17 encapsulating the sterilizing fluid without also puncturing at least one of the chambers 17. In the embodiment depicted in FIG. 6, there are preferably at least 500 chambers 17 throughout the glove 10, and the volume of each chamber 17 is preferably less than one cubic millimeter.

Figure 2:
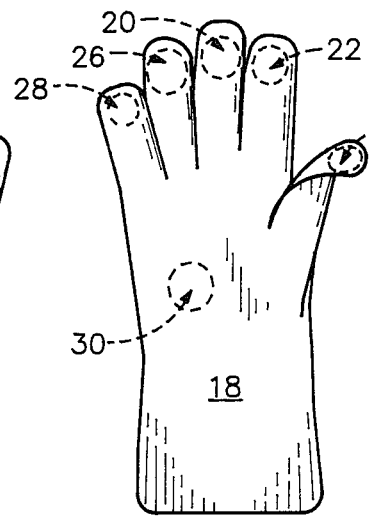
FIG. 2 is a plan view of a glove according to another embodiment of the present invention depicting areas near the glove fingertips that are devoid of any sterilizing fluid.

The glove 18 shown in FIG. 2 may in all respects be similar to the glove 10 shown in FIG. 1 except that certain regions of the glove 18 are devoid of any chambers 12 containing sterilizing fluid so that sensitivity may be maximized in those regions. Specifically, region 20 on the inside tip of the middle finger, region 22 on the inside tip of the index finger, and region 24 on the inside tip of the thumb are all devoid of chambers 12. It will be appreciated that these regions are most often used by doctors during surgery, especially for grasping a scalpel. Alternatively, regions 26, 28 on the inside tip of the ring finger and the little finger, respectively, as well as a region 30 at the heel of the hand (where the heel of a scalpel contacts the hand) may also be devoid of chambers 12 so that only a very thin layer of latex is covering those areas.

Figure 3:
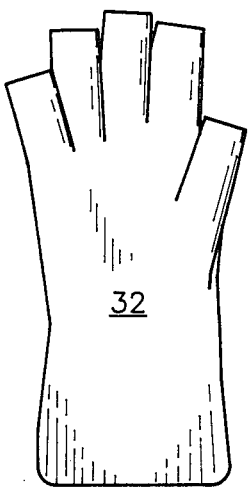
FIG. 3 is a glove according to yet another embodiment of the present invention in which the glove fingertips have been eliminated.

The glove 32 shown in FIG. 3 is in all respects similar to the glove 10 shown in FIG. 1 except that the fingertips and thumb tip of the glove 32 have been eliminated. The glove 32 is especially suited to be worn over a conventional latex glove. Again, the glove 32 helps maximize the sensitivity in those regions of the person's hand used to touch and feed objects.

Although the glove 10 has been described as being fashioned from latex, the present invention contemplates the glove 10 being fashioned from plastics and possibly other materials.

The sterilizing fluid contained in the chambers 12 of the glove 10 of the present invention may comprise a variety of different chemicals and chemical mixtures that are effective in immediately sterilizing contagious disease producing microbes (such as viruses, bacteria and possibly spores) upon contact. In the context of the present invention, the concept of immediate sterilization means that the disease-producing characteristic is rendered ineffective within ten minutes, and preferably within thirty seconds. The disease-producing characteristic can be rendered ineffective by killing the microbe, preventing reproduction of the microbe, or otherwise. In those situations where a patient is known to be infected with a particular disease, the sterilizing fluid can be tailored to provide maximum effectiveness in sterilizing the microbes producing that disease. Otherwise, a more general sterilizing fluid such as a strong bleach solution or a detergent should be used. Care should be taken to insure that the sterilizing fluid will not react with the material from which the glove 10 is fashioned in such a way as to cause the sterilizing fluid to leak from the chambers before the glove 10 is normally used.

Some effective sterilizing fluids are:

| Chemical Compound | Known Minimum Concentration By Volume For Immediately Sterilizing AIDS Virus (HIV-1) | Known Minimum Concentration By Volume For Immediately Sterilizing Hepatitis B Virus |
|---|---|---|
| Ethyl Alcohol | 50% | 80% |
| Isopropyl Alcohol | 30% | 70% |
| NP-40 (ethylphenyl-polyethylene glycol) | 1% | — |
| Hydrogen Peroxide | 0.3% | — |
| Household Bleach | 0.1% | 10% |

Although particular embodiments of the present invention have been described and illustrated herein, it should be recognized that modifications and variations may readily occur to those skilled in the art and that such modifications and variations may be made without departing from the spirit and the scope of my invention. Consequently, my invention as claimed below may be practiced otherwise than is specifically described above.

I claim:

1. A glove for inhibiting the spread of a contagious disease to a person handling the body fluid of a person infected with the disease, and said glove possessing a first array of chambers arranged substantially side by side in a first substantially uniform layer and a second array of chambers arranged substantially side by side in a second substantially uniform layer, said first layer substantially immediately adjacent to and below said second layer, and said chambers of said first array arranged in a staggered relation relative to said chambers of said second array, said chambers containing a sterilizing fluid capable of substantially immediately sterilizing the microbes causing said disease substantially upon contact.

2. A glove according to claim 1 having open ended fingers whereby the glove is adapted to expose the person's fingertips.

3. A glove according to claim 1 wherein said chambers extend substantially throughout the entire glove except substantially in the region of the glove thumbtip, the region of the glove index fingertip, and at least part of the region of the glove heel.

4. A glove according to claim 1 wherein said chambers extend substantially throughout the entire glove except substantially in the region of the glove thumbtip, the region of the glove index fingertip, and the region of the glove middle fingertip.

5. A glove according to claim 1 wherein said chambers extend substantially throughout the entire glove except substantially in the region of the glove fingertips.

6. A glove according to claim 1 wherein the thickness of said glove is substantially in the range of one millimeter to five millimeters.

7. A glove according to claim 1 wherein said chambers number substantially in the range of between fifty and five hundred.

8. A glove according to claim 7 wherein the volume of substantially each said chamber is less than two cubic centimeters.

9. A glove according to claim 1 wherein said chambers number at least five hundred and wherein the volume of substantially each said chamber is less than one cubic millimeter.

10. A glove according to claim 1 fashioned of a flexible, stretchable material.

11. A glove according to claim 1 comprising an outer sheath and an inner sheath adapted to be disposed immediately adjacent to the person's hand, said arrays of chambers being interposed between said outer sheath and said inner sheath, the thickness of said outer sheath being thinner than the thickness of said inner sheath.

12. A glove according to claim 1 wherein said sterilizing fluid is capable of substantially immediately sterilizing microbes that cause Acquired Immunodeficiency Syndrome (AIDS).

13. A glove according to claim 1 wherein said sterilizing fluid is capable of substantially immediately sterilizing microbes producing Hepatitis.

14. A glove according to claim 1 wherein said sterilizing fluid comprises bleach.

15. A glove according to claim 1 wherein said sterilizing fluid comprises detergent.

16. A glove according to claim 1 wherein said sterilizing fluid comprises ethyl alcohol.

17. A glove according to claim 1 wherein said sterilizing fluid comprises isopropyl alcohol.

18. A glove according to claim 1 wherein said sterilizing fluid comprises NP-40.

19. A glove according to claim 1 wherein said sterilizing fluid comprises hydrogen peroxide.

20. A method of inhibiting the spread of a contagious disease to a person handling the body fluid of a person undergoing a medical operation who is infected with the disease comprising the steps of:
providing a glove possessing a first array of chambers arranged substantially side by side in a first substantially uniform layer and a second array of chambers arranged substantially side by side in a second substantially uniform layer, said first layer substantially immediately adjacent to and below said second layer, and said chambers of said first array arranged in a staggered relation relative to said chambers of said second array, said chambers containing a sterilizing fluid capable of substantially immediately sterilizing the microbes causing said disease substantially upon contact; and
wearing said glove on the hand of the person handling the body fluid during the operation.

21. A glove for inhibiting the spread of a contagious disease to a person handling the body fluid of a person infected with the disease, said glove possessing a plurality of chambers numbering at least five hundred and wherein the volume of substantially each said chamber is less than one cubic millimeter, said chambers containing a sterilizing fluid capable of substantially immediately sterilizing the microbes causing said disease substantially upon contact.

22. A glove according to claim 21 having open ended fingers whereby the glove is adapted to expose the person's fingertips and thumbtip.

23. A glove according to claim 21 wherein said chambers extend substantially throughout the entire glove except substantially in the region of the glove thumbtip, the region of the glove index fingertip, and at least a part of the region of the glove heel.

24. A glove according to claim 21 wherein said chambers extend substantially throughout the entire glove except substantially in the region of the glove thumbtip, the region of the glove index fingertip, and the region of the glove middle fingertip.

25. A glove according to claim 21 wherein said chamber extends substantially throughout the entire glove except substantially in the region of the glove fingertips.

26. A glove according to claim 21 wherein the thickness of said glove is substantially in the range of one millimeter to five millimeters.

27. A glove according to claim 21 fashioned of a flexible, stretchable material.

28. A glove according to claim 21 wherein said sterilizing fluid is capable of substantially immediately sterilizing microbes that cause Acquired Immunodeficiency Syndrome (AIDS).

29. A glove according to claim 21 wherein said sterilizing fluid is capable of substantially immediately sterilizing microbes producing Hepatitis.

30. A glove according to claim 21 wherein said sterilizing fluid comprises bleach.

31. A glove according to claim 21 wherein said sterilizing fluid comprises detergent.

32. A glove according to claim 21 wherein said sterilizing fluid comprises ethyl alcohol.

33. A glove according to claim 21 wherein said sterilizing fluid comprises isopropyl alcohol.

34. A glove according to claim 21 wherein said sterilizing fluid comprises NP-40.

35. A glove according to claim 21 wherein said sterilizing fluid comprises hydrogen peroxide.

36. A method of inhibiting the spread of a contagious disease to a person handling the body fluid of a person undergoing a medical operation who is infected with the disease comprising the steps of:
providing a glove possessing a plurality of chambers numbering at least five hundred and wherein the volume of substantially each said chamber is less than one cubic millimeter, said chambers containing a sterilizing fluid capable of substantially immediately sterilizing the microbes causing said disease substantially upon contact; and
wearing said glove on the hand of the person handling the body fluid during the operation.

37. A glove for inhibiting the spread of a contagious disease to a person handling the body fluid of a person infected with the disease, said glove possessing at least one chamber containing a sterilizing fluid capable of substantially immediately sterilizing the microbes causing said disease substantially upon contact, said glove having open ended fingers whereby the glove is adapted to expose the person's fingertips and thumbtip.

* * * * *